US009901272B2

United States Patent
Youn et al.

(10) Patent No.: US 9,901,272 B2
(45) Date of Patent: Feb. 27, 2018

(54) APPARATUS AND METHOD FOR MEASURING ELECTROCARDIOGRAM USING WIRELESS COMMUNICATION

(71) Applicant: KOREA INSTITUTE OF SCIENCE AND TECHNOLOGY, Seoul (KR)

(72) Inventors: Inchan Youn, Seoul (KR); Kuiwon Choi, Seoul (KR); Jun-Kyo Francis Suh, Seoul (KR); Seung-Jong Kim, Seoul (KR); Hyung Min Kim, Seoul (KR); Youn Joo Lee, Seoul (KR); Inwon Jung, Seoul (KR); Heesu Park, Seoul (KR); Sunghee Park, Seoul (KR); Jeong Hwan Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 28 days.

(21) Appl. No.: 15/185,454

(22) Filed: Jun. 17, 2016

(65) Prior Publication Data
US 2017/0055862 A1 Mar. 2, 2017

(51) Int. Cl.
*A61B 5/0428* (2006.01)
*A61B 5/0402* (2006.01)
*A61B 5/00* (2006.01)

(52) U.S. Cl.
CPC .......... *A61B 5/0402* (2013.01); *A61B 5/0006* (2013.01); *A61B 5/6824* (2013.01); *A61B 5/6828* (2013.01); *A61B 5/6829* (2013.01); *A61B 5/6831* (2013.01); *A61B 5/725* (2013.01);
(Continued)

(58) Field of Classification Search
CPC . A61B 5/0402; A61B 5/04028; A61B 5/0428; A61B 5/04282
See application file for complete search history.

(56) References Cited

U.S. PATENT DOCUMENTS

| | | | |
|---|---|---|---|
| 8,831,715 B2 | 9/2014 | Boege et al. | |
| 8,838,218 B2 | 9/2014 | Khair | |
| 2007/0179376 A1* | 8/2007 | Gerder ................. | A61B 5/0006 600/393 |

FOREIGN PATENT DOCUMENTS

| | | |
|---|---|---|
| EP | 1 611 833 A1 | 1/2006 |
| KR | 10-2008-0084880 A | 9/2008 |
| KR | 10-0927471 B1 | 11/2009 |

(Continued)

*Primary Examiner* — George Evanisko
(74) *Attorney, Agent, or Firm* — NSIP Law (57) ABSTRACT

Disclosed is an apparatus for measuring electrocardiogram (ECG) using wireless communication, including a first measuring device and a second measuring device connected to each other using wireless communication, wherein the first measuring device includes a first electrode configured to measure a first signal generated by a heartbeat, and a slave signal generation unit configured to generate a slave signal based on the first signal and a wireless virtual ground signal received from the second measuring device, and the second measuring device includes a second electrode configured to measure a second signal generated by a heartbeat, a ground electrode configured to measure a ground signal, a wireless virtual ground unit configured to generate the wireless virtual ground signal based on the ground signal, and an ECG measuring unit configured to measure ECG based on the slave signal, the second signal, and the wireless virtual ground signal.

18 Claims, 6 Drawing Sheets

(52) U.S. Cl.
CPC .......... *A61B 5/7225* (2013.01); *A61B 5/7278* (2013.01); *A61B 5/742* (2013.01); *A61B 5/7475* (2013.01)

(56) References Cited

FOREIGN PATENT DOCUMENTS

| | | |
|---|---|---|
| KR | 10-1012810 B1 | 2/2011 |
| KR | 10-1375443 B1 | 3/2014 |
| KR | 10-2014-0124377 A | 10/2014 |
| KR | 10-2014-0124455 A | 10/2014 |
| KR | 10-2014-0144009 A | 12/2014 |
| WO | WO 2008/120950 A1 | 10/2008 |
| WO | WO 2012/019760 A1 | 2/2012 |
| WO | WO 2013/109154 A1 | 7/2013 |

\* cited by examiner

APPARATUS AND METHOD FOR MEASURING ELECTROCARDIOGRAM USING WIRELESS COMMUNICATION

CROSS-REFERENCE TO RELATED APPLICATION

This application claims priority to Korean Patent Application No. 10-2015-0118548, filed on Aug. 24, 2015, and all the benefits accruing therefrom under 35 U.S.C. § 119, the contents of which in its entirety are herein incorporated by reference.

BACKGROUND

1. Field

The present disclosure relates to an apparatus and method for measuring electrocardiogram (ECG) using wireless communication, and more particularly, to an apparatus and method for measuring ECG using wireless communication in which an ECG is measured based on electrical signals measured at different locations and transmitted using wireless communication.

DESCRIPTION ABOUT NATIONAL RESEARCH AND DEVELOPMENT SUPPORT

This study was supported by the Bio Medical Technology Development Project—Leading Research Support Project of Ministry of Science, ICT and Future Planning, Republic of Korea (Life guardians-based stress measurement/management system development using dual-band, Project No. 1711018655) under the Korea Institute of Science and Technology.

2. Description of the Related Art

An electrocardiogram (ECG) is a recording of heartbeat-related potentials measured on the surface of the body, and is often used in clinic practice because it can be measured through a non-invasive test without any pain or side effect in a subject.

Generally, a plurality of electrodes attached to the body to measure ECG is connected to each other with wired connection. Thus, there is a problem with activity restriction of a subject during measurement of heart rate.

SUMMARY

In this context, the present disclosure is designed to solve the problem, and therefore, the present disclosure is directed to providing an apparatus and method for measuring electrocardiogram (ECG) using wireless communication, in which heart rate is wirelessly measured by connecting electrodes for measuring the heart rate to each other using wireless communication.

An apparatus for measuring ECG using wireless communication according to an embodiment for achieving the object of the present disclosure includes a first measuring device and a second measuring device connected to each other using wireless communication, and the first measuring device includes a first electrode configured to measure a first signal generated by a heartbeat, and a slave signal generation unit configured to generate a slave signal based on the first signal and a wireless virtual ground signal received from the second measuring device, and the second measuring device includes a second electrode configured to measure a second signal generated by a heartbeat, a ground electrode configured to measure a ground signal, a wireless virtual ground unit configured to generate the wireless virtual ground signal based on the ground signal, and an ECG measuring unit configured to measure ECG based on the slave signal, the second signal, and the wireless virtual ground signal.

In an embodiment of the present disclosure, the wireless virtual ground unit may provide a virtual ground for matching reference voltages of the signals between the first measuring device and the second measuring device, and the slave signal generation unit may generate the slave signal using the wireless virtual ground signal as reference voltage.

In an embodiment of the present disclosure, the ECG measuring unit may include a differential amplifier to amplify a difference between the slave signal and the second signal using the wireless virtual ground signal as reference voltage.

In an embodiment of the present disclosure, the ECG measuring unit may further include a signal processing unit to filter and amplify a signal outputted from the differential amplifier, and the signal processing unit may include a high pass filter, a low pass filter, a notch filter, and a signal amplifier.

In an embodiment of the present disclosure, the second measuring device may further include a synchronization control unit to synchronize phases between the slave signal and the second signal.

In an embodiment of the present disclosure, the slave signal may be converted to a digital signal and transmitted from the first measuring device to the second measuring device, and the wireless virtual ground signal may be converted to a digital signal and transmitted from the second measuring device to the first measuring device.

In an embodiment of the present disclosure, the first signal may be measured at a wrist or an arm on any one of left and right sides, and the second signal may be measured at a wrist or an arm on the other one of left and right sides.

In an embodiment of the present disclosure, any one of the first signal and the second signal may be measured at a left leg or a left ankle, and the other one of the first signal and the second signal may be measured at a wrist or an arm on any one of left and right sides.

In an embodiment of the present disclosure, each of the first measuring device and the second measuring device may include a band part having a ring shape.

A method for measuring ECG using wireless communication according to an embodiment for achieving the object of the present disclosure measures ECG using a first measuring device and a second measuring device connected to each other using wireless communication, and includes measuring a first signal generated by a heartbeat using the first measuring device and measuring a second signal generated by a heartbeat and a ground signal using the second measuring device, generating a wireless virtual ground signal based on the ground signal and transmitting the wireless virtual ground signal from the second measuring device to the first measuring device, generating a slave signal based on the first signal and the wireless virtual ground signal received from the second measuring device and transmitting the generated slave signal from the first measuring device to the second measuring device, and measuring ECG based on the wireless virtual ground signal, the second signal, and the slave signal received from the first measuring device.

In an embodiment of the present disclosure, the wireless virtual ground signal may provide a virtual ground for matching reference voltages of the signals between the first measuring device and the second measuring device, and the slave signal may be generated using the wireless virtual ground signal as reference voltage.

In an embodiment of the present disclosure, the measuring of ECG may include amplifying, using a differential amplifier, a difference between the slave signal and the second signal using the wireless virtual ground signal as reference voltage.

In an embodiment of the present disclosure, the measuring of ECG may further include filtering a signal outputted from the differential amplifier using a high pass filter, a low pass filter, and a notch filter, and amplifying the signal using a signal amplifier.

In an embodiment of the present disclosure, the method for measuring ECG using wireless communication may further include synchronizing phases between the slave signal and the second signal.

In an embodiment of the present disclosure, the slave signal may be converted to a digital signal and transmitted from the first measuring device to the second measuring device, and the wireless virtual ground signal may be converted to a digital signal and transmitted from the second measuring device to the first measuring device.

In an embodiment of the present disclosure, the first signal may be measured at a wrist or an arm on any one of left and right sides, and the second signal may be measured at a wrist or an arm on the other one of left and right sides.

In an embodiment of the present disclosure, any one of the first signal and the second signal may be measured at a left leg or a left ankle, and the other one of the first signal and the second signal may be measured at a wrist or an arm on any one of left and right sides.

According to the apparatus and method for measuring ECG using wireless communication as above, heart rate of a wearer can be measured without activity restriction of the wearer in daily life.

DETAILED DESCRIPTION

Hereinafter, the present disclosure will be described in further detail with reference to the accompanying drawings.

Figure 1:
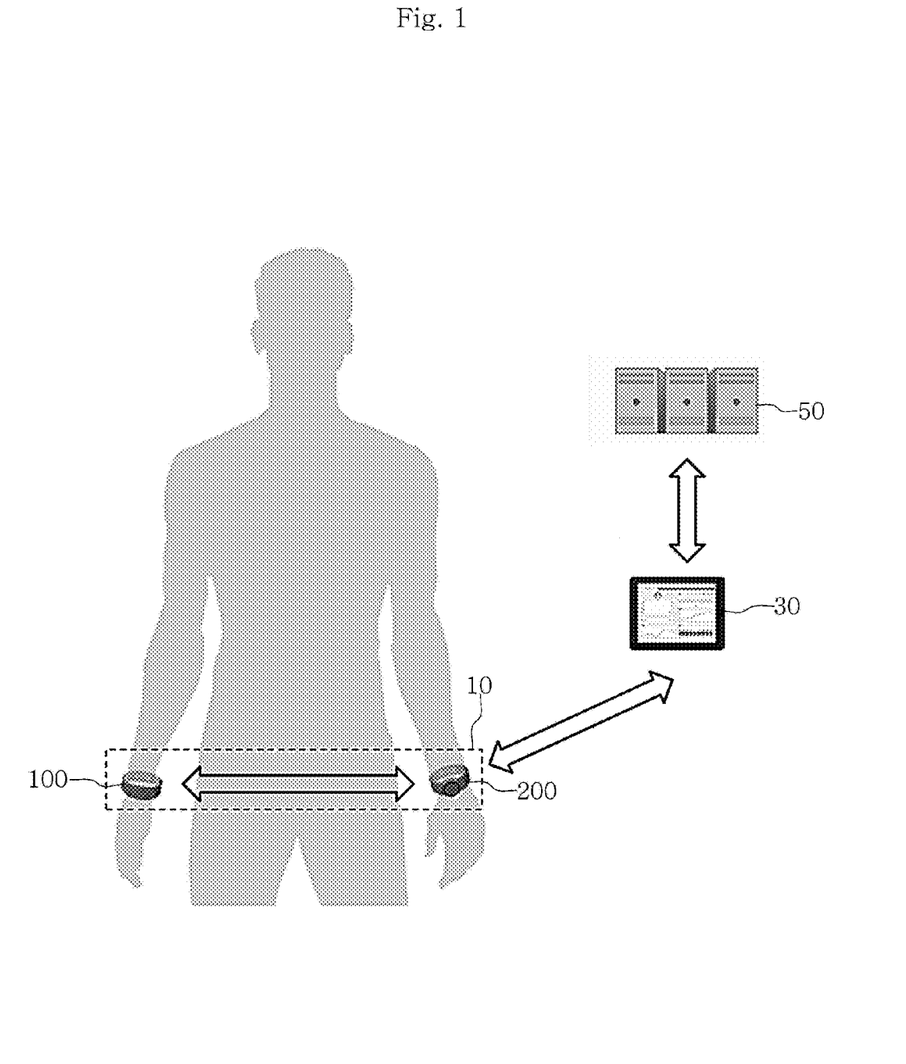
FIG. 1 is a conceptual diagram for describing an electrocardiogram (ECG) measuring apparatus according to an embodiment of the present disclosure.

FIG. 1 is a conceptual diagram for describing an electrocardiogram (ECG) measuring apparatus 10 according to an embodiment of the present disclosure.

Referring to FIG. 1, the ECG measuring apparatus 10 includes a first measuring device 100 and a second measuring device 200 connected to each other using wireless communication.

The ECG measuring apparatus 10 may measure ECG of a wearer using Lead I, II, and III configuration.

To measure ECG using Lead I configuration, the ECG measuring apparatus 10 may measure potential signals generated by heartbeats from two wrists or arms of the wearer using the first and second measuring devices 100 and 200, and measure ECG of the wearer using the measured potential signals.

In the case of measuring ECG using Lead I configuration, the potential signals generated by heartbeats may include, for example, a first signal measured at any one of a right arm and a right wrist, a second signal measured at any one of a left arm and a left wrist, and a ground signal which is a reference for the first signal and the second signal. The ground signal may be measured at any one of a wrist and an arm on any one of left and right sides.

To measure ECG using Lead II configuration, the ECG measuring apparatus 10 may measure potential signals generated by heartbeats from a left leg (or a left ankle) and a right arm (or a right wrist) of the wearer using the first and second measuring devices 100 and 200, and measure ECG of the wearer using the measured potential signals.

In the case of measuring ECG using Lead II configuration, the potential signals generated by heartbeats may include, for example, a first signal measured at any one of a right arm and a right wrist, a second signal measured at any one of a left leg and a left ankle, and a ground signal which is a reference for the first signal and the second signal. The ground signal may be measured at any one of a right arm, a right wrist, a left leg, and a left ankle.

To measure ECG using Lead III configuration, the ECG measuring apparatus 10 may measure potential signals generated by heartbeats from a left leg (or a left ankle) and a left arm (or a left wrist) of the wearer using the first and second measuring devices 100 and 200, and measure ECG of the wearer using the measured potential signals.

In the case of measuring ECG using Lead III configuration, the potential signals generated by heartbeats may include, for example, a first signal measured at any one of a left arm and a left wrist, a second signal measured at any one of a left leg and a left ankle, and a ground signal which is a reference for the first signal and the second signal. The ground signal may be measured at any one of a left arm, a left wrist, a left leg, and a left ankle.

Hereinafter, the first measuring device 100 and the second measuring device 200 are described based on Lead I configuration in which each measuring device is worn on two wrists of a user, but is not limited thereto. In other embodiments, the first measuring device 100 and the second measuring device 200 may be worn on two arms, or any one of the first and second measuring devices 100 and 200 may be worn on a wrist and the other may be worn on an arm. In other embodiments, any one of the first measuring device 100 and the second measuring device 200 may be worn on a right arm or a right wrist of a user and the other may be worn on a left leg or a left ankle (Lead II configuration), and any one of the first measuring device 100 and the second measuring device 200 may be worn on a left arm or a left wrist of a user and the other may be worn on a left leg or a left ankle (Lead III configuration).

In an embodiment, the first measuring device 100 may be worn on a right wrist of the wearer, and the second measuring device 200 may be worn on a left wrist of the wearer. To the contrary, the first measuring device 100 may be worn on a left wrist of the wearer, and the second measuring device 200 may be worn on a right wrist of the wearer.

In an embodiment, to measure potential signals generated by heartbeats from the wrists (or arms, legs or ankles) of the wearer, each of the first measuring device 100 and the second measuring device 200 may include a band part having a ring shape that can be worn on a wrist (or an arm, a leg or an ankle) of a user.

In an embodiment, each of the first measuring device 100 and the second measuring device 200 may further include a display unit to display the measured signals including ECG. The display unit may include a touch screen, and the ECG measuring apparatus 10 may input and output commands or data for controlling the operation of the first and second measuring units 100 and 200 through the display unit.

The ECG measuring apparatus 10 may be connected to an external computing device 30 such as, for example, a mobile device, a PC, a laptop computer, and a smart TV using wired or wireless communication. The computing device 30 may receive measured data including the ECG measured from the ECG measuring apparatus 10 or the potential signals generated by heartbeats, and transmit or receive commands relating to ECG measurement. The computing device 30 may analyze bio-signals of the wearer using the measured data received from the ECG measuring apparatus 10, and display the analyzed results through a display.

The computing device 30 may communicate with a database server 50 which stores database relating to ECG, to analyze the measured data. The database for analyzing the measured data may be included in the computing device 30.

Hereinafter, the present disclosure is described based on the case in which the first measuring device 100 is worn on a right wrist of the wearer, and the second measuring device 200 is worn on a left wrist of the wearer, but is not limited thereto.

Figure 2:
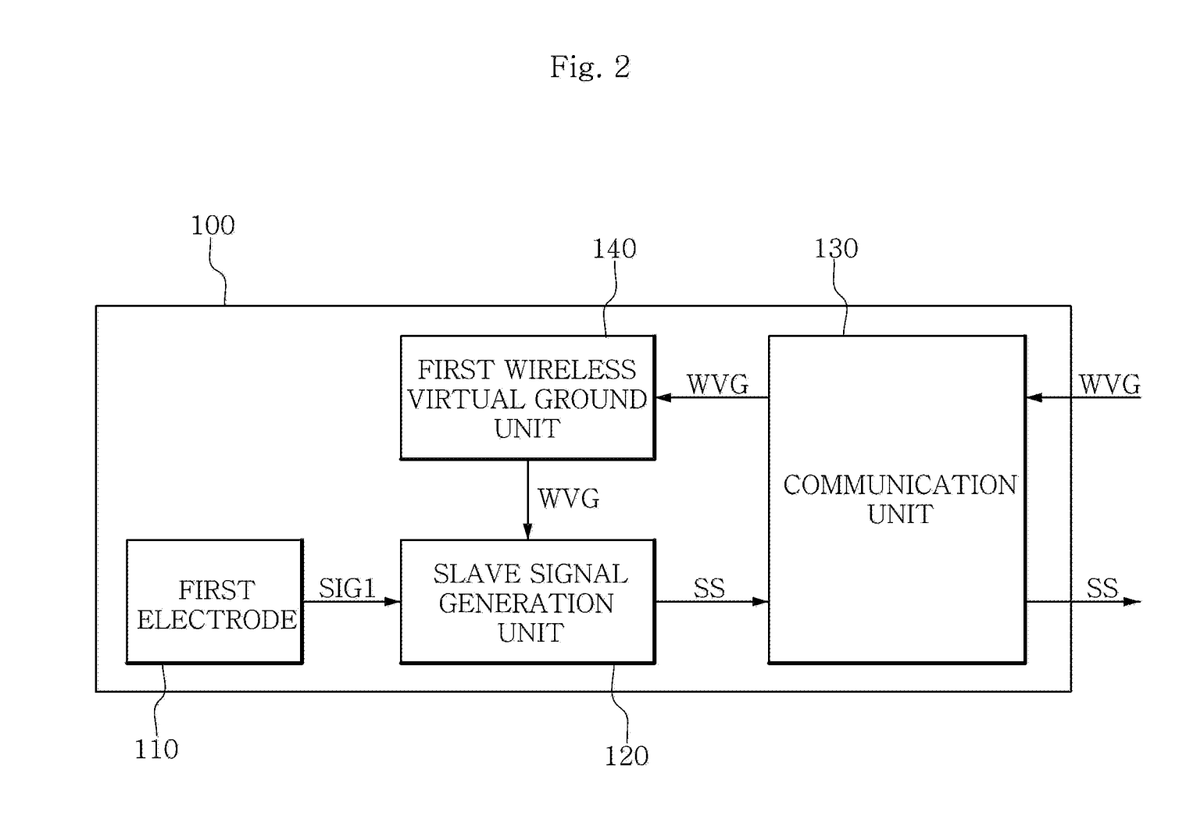
FIG. 2 is a block diagram showing a first measuring device of FIG. 1.
Figure 3:
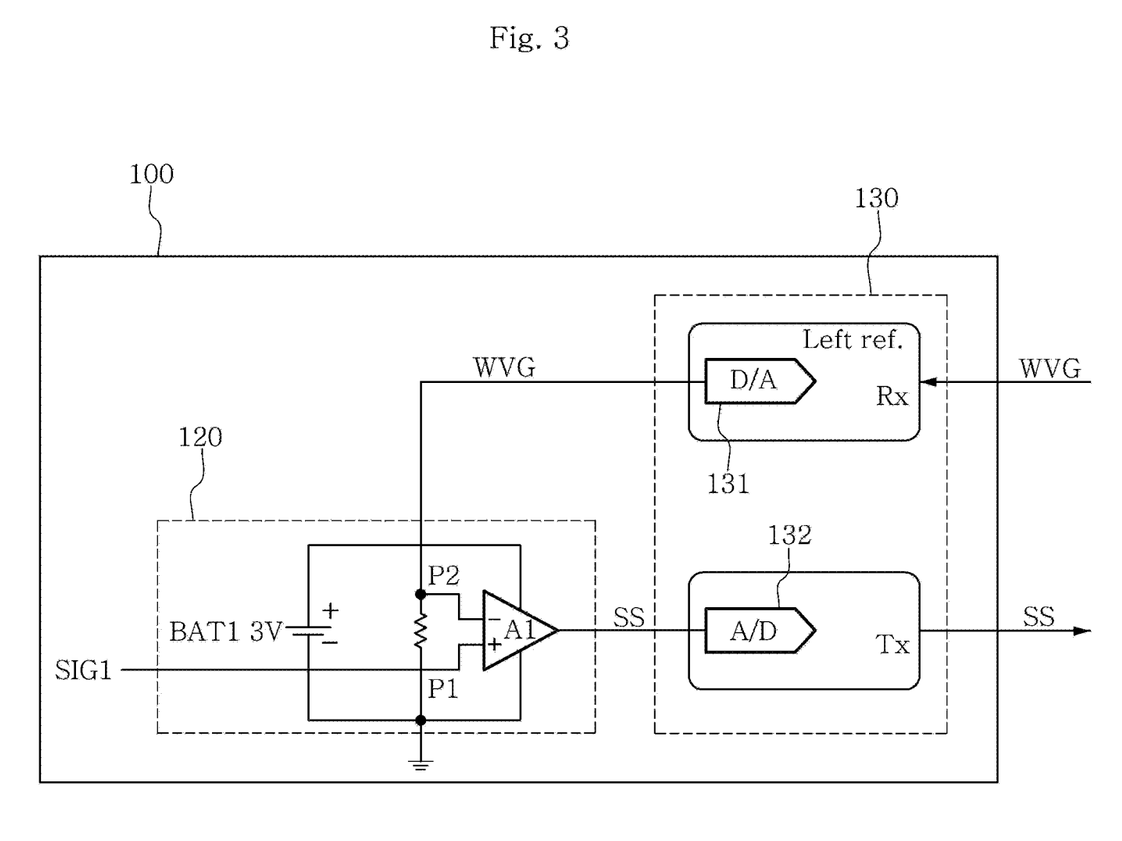
FIG. 3 is a conceptual diagram for describing a first measuring device of FIG. 2.

FIG. 2 is a block diagram showing the first measuring device 100 of FIG. 1. FIG. 3 is a conceptual diagram for describing the first measuring device of FIG. 2.

Referring to FIGS. 1 through 3, the first measuring device 100 includes a first electrode 110, a slave signal generation unit 120, and a communication unit 130.

The first electrode 110 may measure a first signal SIG1. In an embodiment, the first electrode 110 may measure a first signal SIG1 from the right wrist of the wearer. The first signal SIG1 may include an electrical signal generated by a heartbeat.

The slave signal generation unit 120 may match reference voltage of the first signal SIG1 measured by the first electrode 110 to reference voltage of the signal measured by the second measuring device 200, to generate a slave signal SS. To adjust the reference voltage of the first signal SIG1, a wireless virtual ground signal WVG received from the second measuring device 200 may be used as reference voltage. The wireless virtual ground signal WVG will be described in detail with reference to FIGS. 4 and 5 together with the second measuring device 200.

The slave signal generation unit 120 may receive an input of the first signal SIG1 through a first input terminal P1, and an input of the wireless virtual ground signal WVG through a second input terminal P2. The slave signal generation unit 120 may generate a slave signal SS based on the received first signal SIG1 and wireless virtual ground signal WVG. In an embodiment, the slave signal generation unit 120 may include an amp A1 to receive an input of the first signal SIG1 through the first input terminal P1 and an input of the wireless virtual ground signal WVG through the second input terminal P2.

The communication unit 130 may transmit signals to the second measuring device 200 and receive signals from the second measuring device 200 using wireless communication. For example, the communication unit 130 may receive (Rx) the wireless virtual ground signal WVG from the second measuring device 200, and transmit (Tx) the slave signal SS to the second measuring device 200.

In an embodiment, the slave signal SS may be converted to a digital signal and transmitted from the first measuring device 100 to the second measuring device 200, and the wireless virtual ground signal WVG may be converted to a digital signal and transmitted from the second measuring device 200 to the first measuring device 100.

The first measuring device 100 may further include a digital-analog converter 131 to convert, to an analog signal, the wireless virtual ground signal WVG converted to the digital signal and received from the second measuring device 200, and an analog-digital converter 132 to convert the slave signal SS to a digital signal.

The first measuring device 100 may further include a first wireless virtual ground unit 140. The first wireless virtual ground unit 140 may provide a virtual ground for matching the reference voltages of the signals between the first measuring device 100 and the second measuring device 200. For example, the first wireless virtual ground unit 140 may output the wireless virtual ground signal WVG received from the second measuring device 200 through the communication unit 130, to the second input terminal P2 of the slave signal generation unit 120. The first wireless virtual ground unit 140 may adjust the wireless virtual ground signal WVG to make the reference voltage of the first signal SIG1 measured by the first electrode 110 correspond to the reference voltage of the signal measured by the second measuring device 200.

Figure 4:
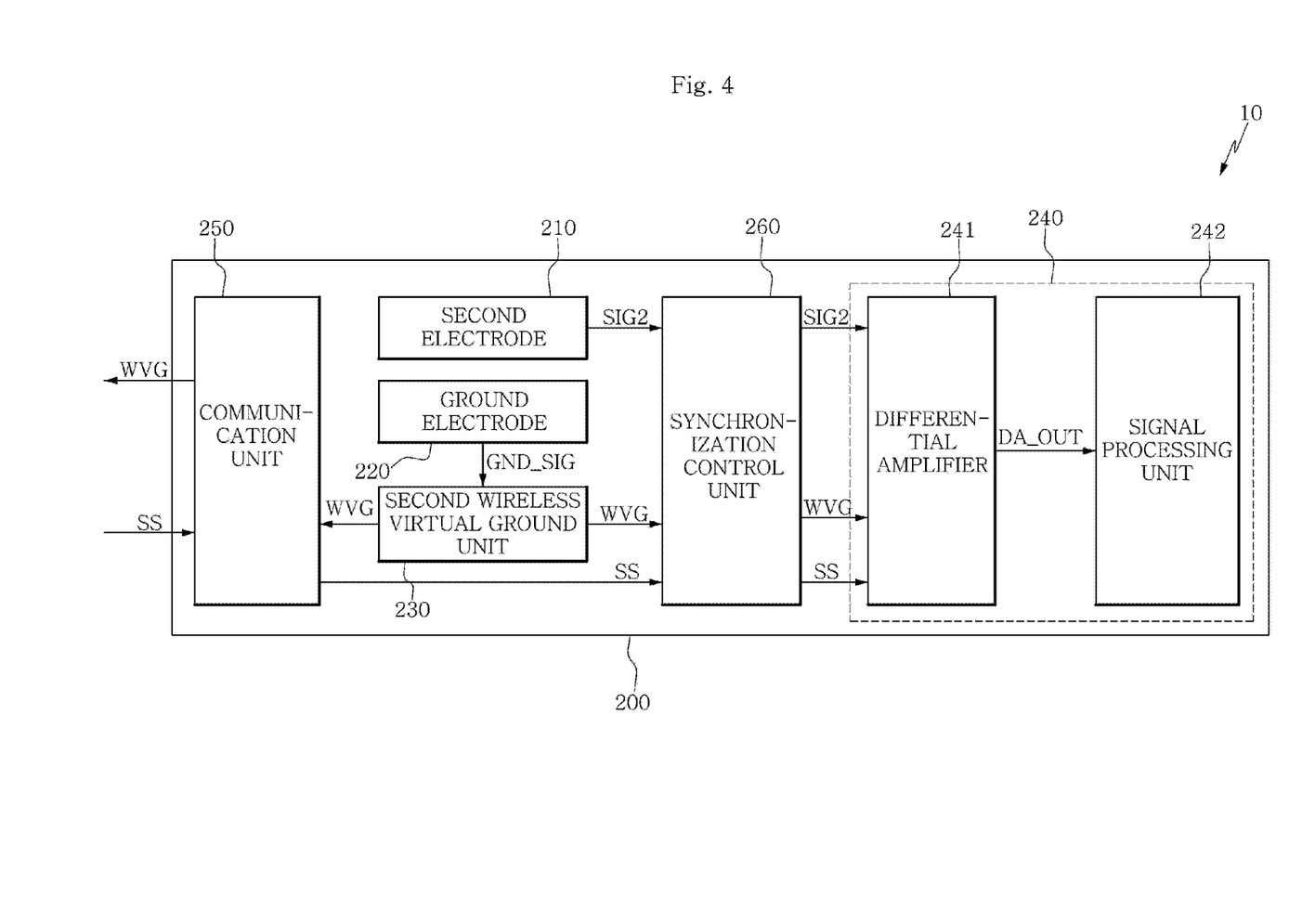
FIG. 4 is a block diagram showing a second measuring device of FIG. 1.
Figure 5:
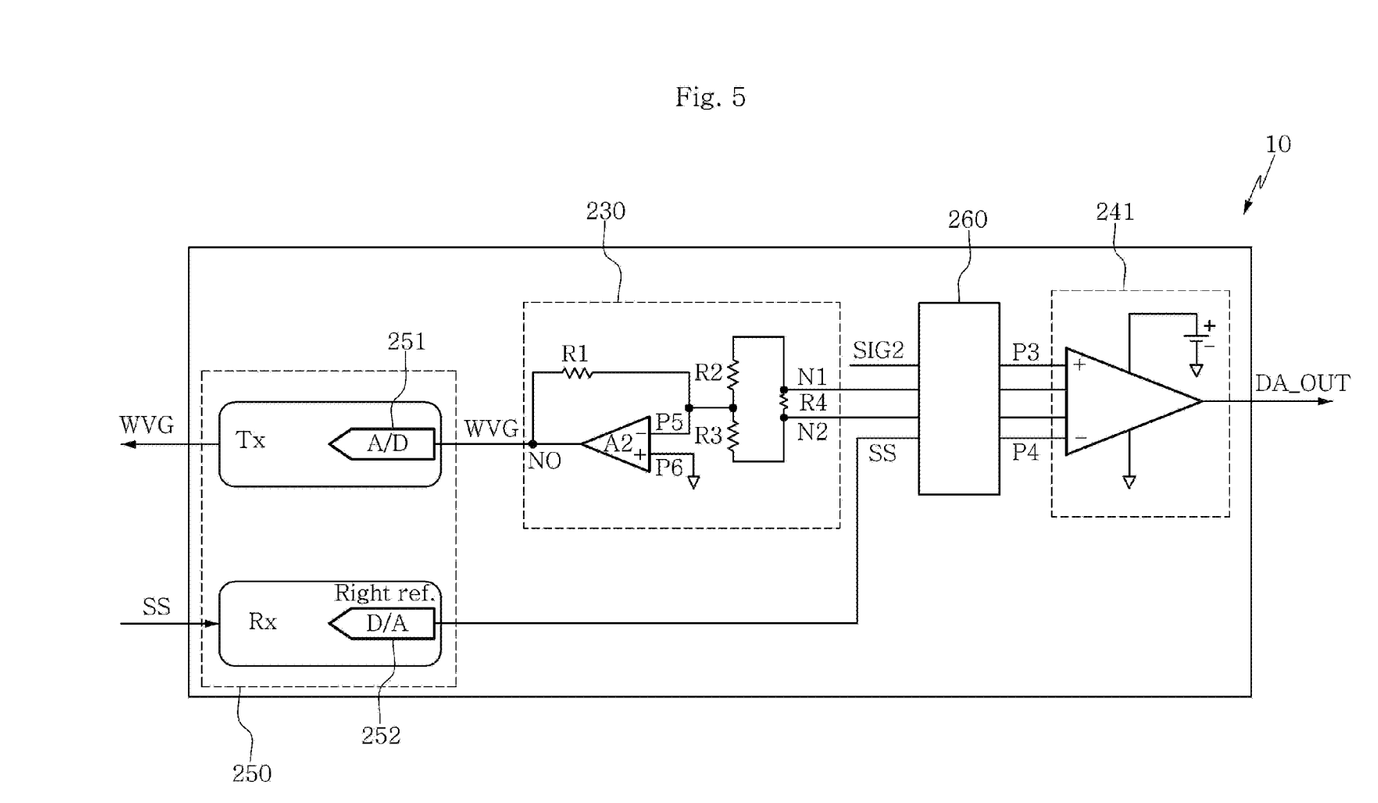
FIG. 5 is a conceptual diagram for describing a second measuring device of FIG. 4.
Figure 6:
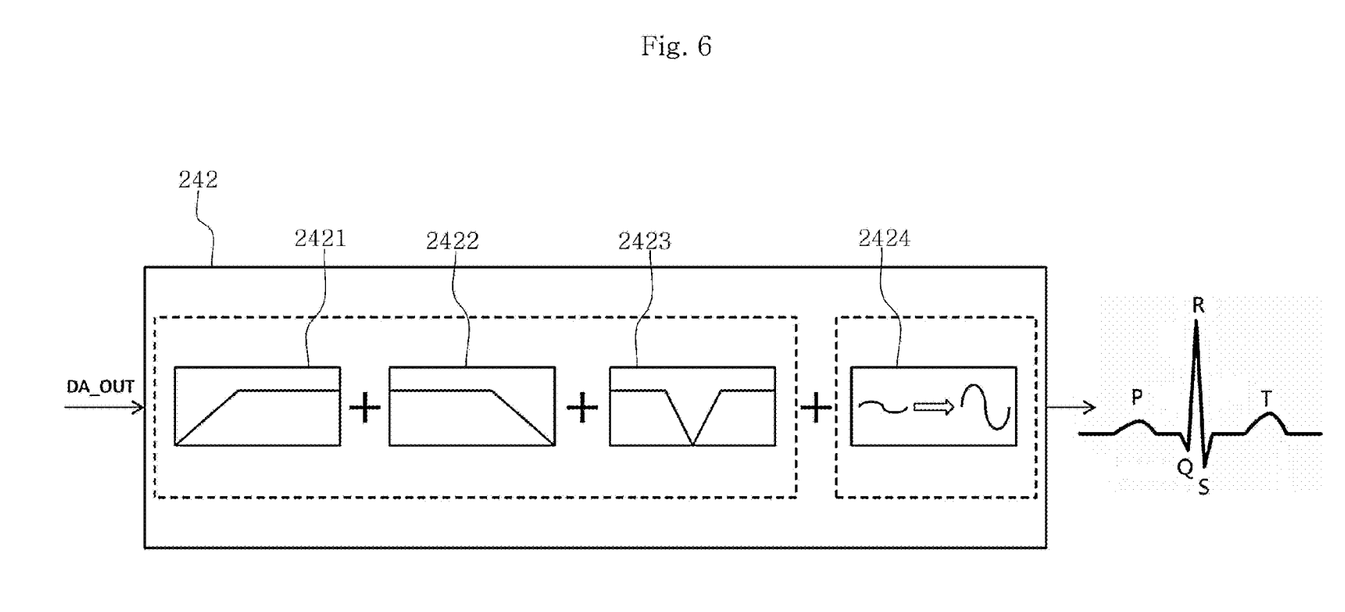
FIG. 6 is a conceptual diagram for describing a signal processing unit of a second measuring device of FIG. 4.

FIG. 4 is a block diagram showing the second measuring device of FIG. 1. FIG. 5 is a conceptual diagram for describing the second measuring device of FIG. 4. FIG. 6 is a conceptual diagram for describing the signal processing unit of the second measuring device of FIG. 4.

Referring to FIGS. 1 and 4 through 6, the second measuring device 200 includes a second electrode 210, a ground electrode 220, a second wireless virtual ground unit 230, an ECG measuring unit 240, and a communication unit 250.

The second electrode 210 may measure a second signal SIG2. In an embodiment, the second electrode 210 may measure the second signal SIG2 from the left wrist of the wearer. The second signal SIG2 may include an electrical signal generated by a heartbeat.

The ground electrode 220 may measure a ground signal GND_SIG. In an embodiment, the ground electrode 220 may measure the ground signal GND_SIG from the left wrist of the wearer. The ground signal GND_SIG may be used as reference voltage of the system power of the second measuring device 200.

The second wireless virtual ground unit 230 may provide a virtual ground for matching reference voltages of the signals between the first measuring device 100 and the second measuring device 200. To provide a virtual ground, the second wireless virtual ground unit 230 may generate a wireless virtual ground signal WVG based on the ground signal GND_SIG measured by the ground electrode 220.

In an embodiment, the second wireless virtual ground unit 230 may include an amp A2, a first resistor R1, a second resistor R2, a third resistor R3, and a fourth resistor R4. The first resistor R1 may be connected between an output terminal NO and a first input terminal P5 of the amp A2. The second resistor R2 may be connected between the first input terminal P5 of the amp A2 and a first node N1. The third resistor R3 may be connected between the first input terminal P5 of the amp A2 and a second node N2. The fourth resistor R4 may be connected between the first node N1 and the second node N2.

The wireless virtual ground signal WVG may be used as reference voltage for the first signal SIG1 and the second signal SIG2. The wireless virtual ground signal WVG may be transmitted to the first measuring device 100 through the communication unit 250 and used as reference voltage for generation of the slave signal SS. In addition, the wireless virtual ground signal WVG may be used as reference voltage for ECG measurement by the ECG measuring unit 240.

The ECG measuring unit 240 may measure ECG based on the slave signal SS received from the first measuring device 100, the second signal SIG2 measured by the second electrode 210, and the wireless virtual ground signal WVG generated by the second wireless virtual ground unit 230.

The ECG measuring unit 240 may include a differential amplifier 241 and a signal processing unit 242.

The differential amplifier 241 may amplify a difference between the slave signal SS and the second signal SIG2 using the wireless virtual ground signal WVG as reference voltage, and output a differential amplification signal DA_OUT. In an embodiment, the differential amplifier 241 may receive an input of the second signal SIG2 through a first input terminal P3 and an input of the slave signal SS through a second input terminal P4. In addition, the differential amplifier 241 is connected to the second wireless virtual ground unit 230 and may use the wireless virtual ground signal WVG as reference voltage. The differential amplifier 241 may amplify a difference between the received second signal SIG2 and slave signal SS to generate a differential amplification signal DA_OUT, and transmit the generated differential amplification signal DA_OUT to the signal processing unit 242.

The signal processing unit 242 may measure ECG by filtering and amplifying the differential amplification signal DA_OUT. The signal processing unit 242 may include a high pass filter 2421, a low pass filter 2422, and a notch filter 2423 to filter the differential amplification signal DA_OUT, and a signal amplifier 2424 to amplify the differential amplification signal DA_OUT. As shown in FIG. 6, the signal processing unit 242 may process the differential amplification signal DA_OUT using the filters 2421, 2422, 2423 and the signal amplifier 2424 to generate an ECG signal consisting of PQRST waves.

The communication unit 250 may transmit signals to the first measuring device 100 and receive signals from the first measuring device 100 using wireless communication. For example, the communication unit 250 may receive (Rx) the slave signal SS from the first measuring device 100, and transmit (Tx) the wireless virtual ground signal WVG to the first measuring device 100.

The communication unit 130 of the first measuring device 100 and the communication unit 250 of the second measuring device 200 may be connected to each other, for example, using short-range wireless communication technology such as Bluetooth communication, infrared (IR) communication, or ZigBee communication. In an embodiment, each of the communication unit 130 of the first measuring device 100 and the communication unit 250 of the second measuring device 200 may include a Bluetooth communication module. For example, the Bluetooth module of the communication unit 130 and the Bluetooth module of the communication unit 250 may be wirelessly connected using Serial Port Profile (SPP) communication.

The second measuring device 200 may further include a digital-analog converter 252 to convert, to an analog signal, the slave signal SS converted to a digital signal and received from the first measuring device 100, and an analog-digital converter 251 to convert the wireless virtual ground signal WVG to a digital signal.

The second measuring device 200 may further include a synchronization control unit 260. The synchronization control unit 260 may synchronize the phases between the second signal SIG2 inputted to the first input terminal P3 of the differential amplifier 241 and the slave signal SS measured from the first measuring device 100 and inputted to the second input terminal P4 of the differential amplifier.

The ECG measuring apparatus according to another embodiment of the present disclosure may include a first measuring device and a second measuring device connected to each other using wireless communication, and the first measuring device and the second measuring device may have the same hardware configuration.

For example, the first measuring device (and the second measuring device) may include a master unit, a slave unit, and a communication unit connected to the master unit and the slave unit. The master unit may include the second electrode 210, the ground electrode 220, the second wireless virtual ground unit 230, the ECG measuring unit 240, the synchronization control unit 260, the analog-digital converter 251, and the digital-analog converter 252 of the second measuring device 200 shown in FIGS. 4 through 6. The slave unit may include the first electrode 110, the slave signal generation unit 120, the first wireless virtual ground unit 140, the digital-analog converter 131, and the analog-digital converter 132 of the first measuring device 100 shown in FIGS. 2 and 3.

The first measuring device and the second measuring device may operate as a master device and a slave device according to settings of the wearer. For example, the slave device may operate as the first measuring device 100 shown in FIGS. 2 and 3, and the master device may operate as the second measuring device 200 shown in FIGS. 4 through 6.

In the case in which the first measuring device (or the second measuring device) operates as a slave device, the salve unit included in the first measuring device (or the second measuring device) may operate with the communication unit, and the master unit may not operate. In contrast, in the case in which the second measuring device (or the first measuring device) operates as a master device, the master unit included in the second measuring device (or the first measuring device) may operate with the communication unit, and the slave unit may not operate. The slave unit and the master unit are substantially the same as the first measuring device 100 and the second measuring device 200 of FIGS. 2 through 6, and an overlapping detailed description may be omitted herein.

While the present disclosure has been hereinabove described with reference to the illustrated embodiments, this is provided for illustration only and it will be understood by those skilled in the art that various variations and modifications in form and details can be made thereto. However, such variations and modifications are intended to be included within the technical scope of protection of the disclosure. Therefore, the genuine technical scope of protection of the disclosure shall be defined by the technical spirit of the appended claims.

What is claimed is:
1. An apparatus for measuring an electrocardiogram (ECG) using wireless communication, the apparatus comprising a first measuring device and a second measuring device connected to each other using wireless communication,
wherein the first measuring device comprises:
a first electrode configured to measure a first signal generated by a heartbeat;

a slave signal generation unit configured to generate a slave signal based on the first signal and a wireless virtual ground signal received from the second measuring device; and a communication unit configured to transmit the slave signal to the second measuring device and to receive the wireless virtual ground signal from the second measuring device, and the second measuring device comprises:

a second electrode configured to measure a second signal generated by a heartbeat;

a ground electrode configured to measure a ground signal;

a wireless virtual ground unit configured to generate the wireless virtual ground signal based on the ground signal;

a second communication unit configured to receive the slave signal from the first measuring device and to transmit the wireless virtual ground signal to the first measuring device and an ECG measuring unit configured to measure the ECG based on the slave signal, the second signal, and the wireless virtual ground signal.

2. The apparatus for measuring the ECG using wireless communication according to claim 1, wherein the wireless virtual ground unit provides a virtual ground for matching reference voltages of the signals between the first measuring device and the second measuring device, and the slave signal generation unit generates the slave signal using the wireless virtual ground signal as reference voltage.

3. The apparatus for measuring the ECG using wireless communication according to claim 2, wherein the ECG measuring unit comprises a differential amplifier to amplify a difference between the slave signal and the second signal using the wireless virtual ground signal as reference voltage.

4. The apparatus for measuring the ECG using wireless communication according to claim 3, wherein the ECG measuring unit further comprises a signal processing unit to filter and amplify a signal outputted from the differential amplifier, and the signal processing unit comprises a high pass filter, a low pass filter, a notch filter, and a signal amplifier connected in series.

5. The apparatus for measuring the ECG using wireless communication according to claim 1, wherein the second measuring device further comprises a synchronization control unit to synchronize phases between the slave signal and the second signal.

6. The apparatus for measuring the ECG using wireless communication according to claim 1, further comprising an analog-digital converter configured to convert the slave signal to a digital signal, and a second analog-digital converter configured to convert the wireless virtual ground signal to a digital signal.

7. The apparatus for measuring the ECG using wireless communication according to claim 1, wherein the first signal is adapted to be measured at a wrist or an arm on one of left and right sides, and the second signal is adapted to be measured at a wrist or an arm on an other one of left and right sides.

8. The apparatus for measuring the ECG using wireless communication according to claim 7, wherein each of the first measuring device and the second measuring device comprises a band part having a ring shape.

9. The apparatus for measuring the ECG using wireless communication according to claim 1, wherein one of the first signal and the second signal is adapted to be measured at a left leg or a left ankle, and an other one of the first signal and the second signal is adapted to be measured at a wrist or an arm on any one of left and right sides.

10. The apparatus for measuring the ECG using wireless communication according to claim 9, wherein each of the first measuring device and the second measuring device comprises a band part having a ring shape.

11. A method for measuring an electrocardiogram (ECG) using wireless communication, which measures ECG using a first measuring device and a second measuring device connected to each other using wireless communication, the method comprising:

measuring a first signal generated by a heartbeat using the first measuring device, and measuring a second signal generated by a heartbeat and a ground signal using the second measuring device;

generating a wireless virtual ground signal based on the ground signal, and transmitting the wireless virtual ground signal from the second measuring device to the first measuring device;

generating a slave signal based on the first signal and the wireless virtual ground signal received from the second measuring device, and transmitting the generated slave signal from the first measuring device to the second measuring device; and measuring the ECG based on the wireless virtual ground signal, the second signal, and the slave signal received from the first measuring device.

12. The method for measuring the ECG using wireless communication according to claim 11, wherein the wireless virtual ground signal provides a virtual ground for matching reference voltages of the signals between the first measuring device and the second measuring device, and the slave signal is generated using the wireless virtual ground signal as reference voltage.

13. The method for measuring the ECG using wireless communication according to claim 12, wherein the measuring of ECG comprises amplifying, using a differential amplifier, a difference between the slave signal and the second signal using the wireless virtual ground signal as reference voltage.

14. The method for measuring the ECG using wireless communication according to claim 13, wherein the measuring of ECG further comprises filtering a signal outputted from the differential amplifier using a high pass filter, a low pass filter, and a notch filter, and amplifying the signal using a signal amplifier.

15. The method for measuring the ECG using wireless communication according to claim 11, further comprising synchronizing phases between the slave signal and the second signal.

16. The method for measuring the ECG using wireless communication according to claim 11, wherein the slave signal is converted to a digital signal and transmitted from the first measuring device to the second measuring device, and the wireless virtual ground signal is converted to a digital signal and transmitted from the second measuring device to the first measuring device.

17. The method for measuring the ECG using wireless communication according to claim 11, wherein the first signal is adapted to be measured at a wrist or an arm on one of left and right sides, and the second signal is adapted to be measured at a wrist or an arm on an other one of left and right sides.

18. The method for measuring the ECG using wireless communication according to claim 11, wherein one of the first signal and the second signal is adapted to be measured at a left leg or a left ankle, and
an other one of the first signal and the second signal is adapted to be measured at a wrist or an arm on one of left and right sides.

* * * * *